United States Patent [19]
Weiss

[11] Patent Number: 4,782,829
[45] Date of Patent: Nov. 8, 1988

[54] APPARATUS FOR PREVENTING BREAKAGE OF BAGS OF TRACHEAL TUBES

[76] Inventor: Sol Weiss, 17227 Queson Pl., Encino, Calif. 91304

[21] Appl. No.: 2,580

[22] Filed: Jan. 12, 1987

[51] Int. Cl.⁴ ............................................. A61M 16/00
[52] U.S. Cl. ............................ 128/200.26; 128/207.15
[58] Field of Search .................... 128/200.26, 207.14, 128/207.15, DIG. 26, 207.16, 207.17

[56] References Cited

U.S. PATENT DOCUMENTS

| | | | |
|---|---|---|---|
| 3,169,529 | 2/1965 | Koenig | 128/207.14 |
| 3,616,799 | 11/1971 | Sparks | 128/207.15 |
| 3,968,800 | 7/1976 | Vilasi | 128/207.14 |
| 4,054,135 | 10/1977 | Berman | 128/207.14 |
| 4,175,564 | 11/1979 | Kwak | 604/171 |
| 4,211,234 | 7/1980 | Fisher | 128/200.26 |
| 4,446,864 | 5/1984 | Watson et al. | 128/207.14 |

OTHER PUBLICATIONS

Passy et al, The KEP Larygeal-Tracheal Stent, Mar. 1971, The Larygscope, pp. 271-275.

Primary Examiner—Edward M. Coven
Assistant Examiner—Timothy G. Philips
Attorney, Agent, or Firm—Gerald L. Price

[57] ABSTRACT

Apparatus for preventing breakage of bags of tracheal tubes comprising a unitary one-piece molded unit having an elongated generally cylindrical longitudinally split main body portion terminating at one end in a restricted opening and at the other end in an open end having an elongated strip extending from one side thereof forming a handle. The handle may be an endless ring connected to the main body portion having its central axis coaxially aligned with the central axis of the main body portion. The main body portion slips over the bag, which is normally deflated, of a tracheal tube prior to insertion of the bag into an incised area or into instruments, the ring providing a handle for removing the apparatus after insertion of the tube to a predetermined depth in the patient thereby preventing breakage of the bag during insertion.

14 Claims, 2 Drawing Sheets

APPARATUS FOR PREVENTING BREAKAGE OF BAGS OF TRACHEAL TUBES

BACKGROUND OF THE INVENTION

1. Field of the Invention

The invention relates to surgical devices; and, more particularly to apparatus for preventing breakage of the bag of a tracheal tube during insertion thereof in an operation.

2. Description of the Prior Art

Tracheal tubes are used in the surgical field in carrying out many operations. Such tubes are used in tracheotomies and have inflatable bags associated therewith. These bags are generally toroidially shaped inflatable bags surrounding the tube and glued thereto and are critical in certain operations. For example, such bags, after insertion of the tube into the patient to a predetermined depth, are inflated to block off the trachea. If gastric juices go around the tracheal tube in any sort of regurgitative process, it can be extremely dangerous to the patient. Also, if foreign objects, such as teeth or other debris, go down into the lung, it can be very dangerous. Thus, such bags are critical in certain operations, such as in cricothrotomies and traceotomies. However, these bags are generally made of thin-walled plastic material, such as polyvinyl, and break or tear easily. Thus, when the tracheal tube is inserted into the incised area of a patient, and/or into other instrumentation used in the operation, the bag can easily be torn by engaging sharp edges of the cartilage of the patient. One such instrumentation is disclosed in U.S. Pat. No. 3,688,773 to Sol Weiss, applicant herein.

Such tubes with the bags attached are quite expensive and must be discarded if the bag tears or is otherwise broken. In addition to the foregoing, such tracheal tubes have varying diameters. For example, most adult tracheal tubes, with which such bags are used, are between 7 to 12 mm in outer diameter. Any means for protecting such bags from breakage should be able to accommodate tracheal tubes within this general area of varying diameters.

There thus exists a need for apparatus for prventing breakage of the bags of tracheal tubes when such tubes are used in operations which apparatus is inexpensive and can be quickly and easily inserted on to tracheal tubes of varying diameters prior to insertion into an incised area or into instrumentation then be withdrawn therefrom after such insertion thereby allowing inflation of the bag.

SUMMARY OF THE INVENTION

It is an object of this invention to provide apparatus for preventing breakage of bags of tracheal tubes during insertion into an incised area or into other instrumentation.

It is a further object of this invention to provide such apparatus which can accommodate tracheal tubes of varying diameters.

It is still further an object of this invention to provide such apparatus which can be quickly and easily placed over the tracheal tube prior to insertion, then removed therefrom after insertion while the tube remains in the incised area or instrumentation.

These and other objects are preferably accomplished by providing a unitary one-piece molded unit having an elongated generally cylindrical longitudinally split main body portion terminating at one end in a restricted opening and at the other end an open end having an elongated strip extending from one side thereof forming a handle. The handle may be an endless ring connected to the main body portion having its central axis coaxially aligned with the central axis of the main body portion. The main body portion slips over the bag, which is normally deflated, of a tracheal tube prior to insertion of the bag into an incised area or into instrumentation, the ring providing a handle for grasping and pulling off the unit from the tube after insertion of the tube to a predetermined depth in the patient while the tube remains in the patient thereby preventing breakage of the bag during insertion. The bag can now be inflated in situ in the patient.

DESCRIPTION OF THE PREFERRED EMBODIMENT

Figure 1:
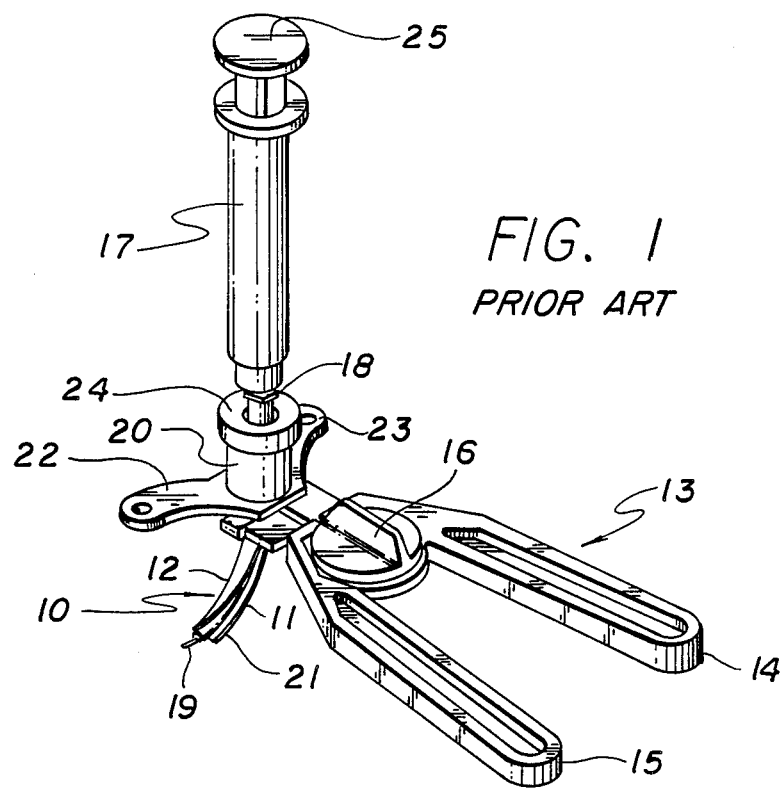
FIG. 1 is a vertical view of a tracheal tube and apparatus for holding the same.

Referring now to FIG. 1 of the drawing, a conventional tracheal tube 10 is shown clasped between needle halves 11, 12 of a tube holder 13 described and claimed in my co-pending application Ser. No. 701,914, filed Feb. 14, 1985 now U.S. Pat. No. 4,643,188, the teachings of which are incorporated herein by reference. Of course, any suitable tube holder may be used.

Thus, holder 13 includes upper and lower handle portions 14, 15 having secured thereto needle halves 11, 12, respectively. As disclosed in my co-pending application, handle portion 14 and needle half 11 is a separate unit from handle portion 15 and needle half 12 held together by a key 16. The connection of such elements is described in detail in my copending application with specific reference to FIG. 1 thereof. Syringe 17 is shown connected to the collar 18 of a stylet 19 extending through tube 10. Tube 10 has an upper cylindrical portion 20 and a lower cylindrical portion 21 of lesser diameter with a throughbore therebetween. Apertured flanges 22, 23 extend from each side of portion 20 at the intersection thereof with lower portion 21 for securing via linear elements in the apertures in flanges 22, 23, tube 10 to the patient. A collar 24 may be provided on the top of portion 20 and syringe 17 may include an obdurator 25.

The foregoing has described the arrangement disclosed in my copending application and reference should be made thereto for detailed description of the elements discussed hereinabove and the use thereon in carrying out tracheotomies and cricothotomies.

Figure 2:
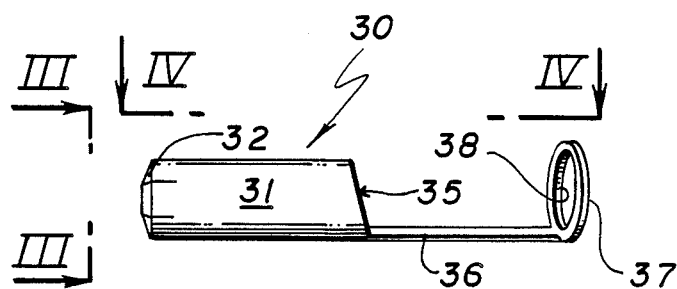
FIG. 2 is a side view of a tracheal tube protector in accordance with the teachings of the invention.
Figure 3:
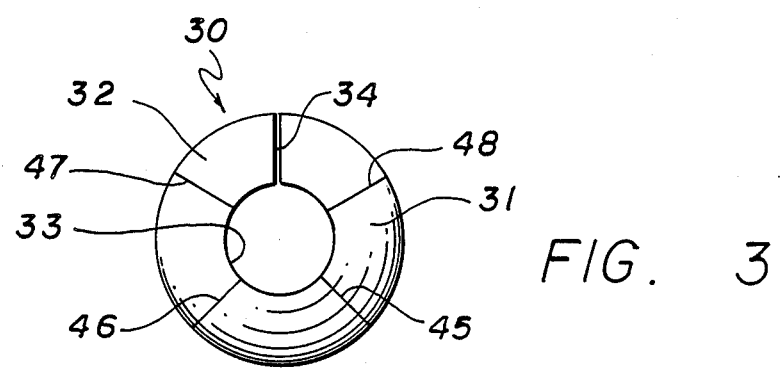
FIG. 3 is a view taken along lines III—III of FIG. 2.
Figure 4:
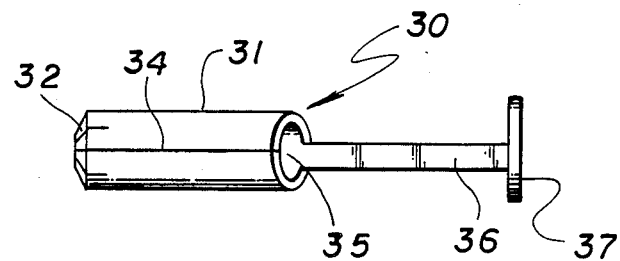
FIG. 4 is a view taken along lines IV—IV of FIG. 2.

As particularly contemplated in the present invention, a tracheal bag protector 30 in accordance with the invention is provided as seen in FIGS. 2 to 6. Protector 30 includes a main generally cylindrical thin walled body portion 31 having a convex rounded front nose 32 at the forward end with a restricted opening 33 therein (FIG. 3). As seen in FIG. 4, a slit 34 is provided along the upper surface of body portion 31 from the forward end of nose 32 (FIG. 3) and rearwardly to open rear end 35 (FIG. 2). A stem or extension member or portion 36, which may be arcuate in cross-section, since, as discussed, it may be cut out from a piece of molded cylindrical material, extends from the bottom of the open end 35 to a terminal ring member 37. Ring member 37 is preferably an endless ring having a circular opening 38 therein with its central axis coincident with the central axis through main body portion 31 and through opening 33 in nose 32.

The ring member 37 is of course preferably formed by cutting out of a section of the aforementioned unitary piece of molded plastic material.

The entire protector 30 may be formed of one unitary piece of resilient material, as heretofore mentioned, such as molded polyethylene plastic material. In this manner, the protector 30 could be made from a single molded plastic cylinder with the cut-out portions and slits as heretofore described. The protector will separate along line 34 and at opening 33 as will be discussed. A plurality of cuts, such as cuts 45 to 48, for example, may be provided in nose 32 surrounding opening 33 as seen in FIG. 3 to further such separation.

Figure 5:
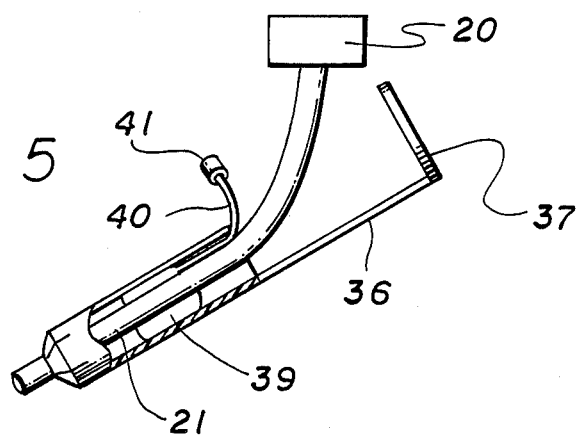
FIG. 5 is a perspective view of a tracheal tube and bag attached thereto showing the protector of FIGS. 2 to 4 installed thereon.

As seen in FIG. 5, the tracheal tube 21 of FIG. 1 is shown prior to insertion into the tube holder 13 as described in my copending application. A conventional toroidially-shaped tracheal bag 39, in its deflated state, surrounds tube 21 and is glued or otherwise secured thereto having an elongated inlet tube 40 extending therefrom and in fluid communication therewith terminating in a one way valve connector end 41. End 41 is adapted to be connected to a syringe (not shown) which can be connected to end 41 to inject air into bag 39 to inflate the same as will be hereinafter discussed.

As seen in FIG. 5, tube 21, with bag 39 attached thereto, has been inserted through open end 35 and out of and through opening 33, slit 34 and cuts 45 to 48 separating to assist in such insertion. Thus, the slits 34 and cuts 45 to 48, and the resiliency of protector 30 not only serve to facilitate such separation but permit protector 30 to accommodate itself to tracheal tubes of varying diameters. That is, tube 21 may be of any outer diameter enabling it to be inserted into protector 30 with body portion 31 accommodating the same due to its inner diameter and resiliency and separation as heretofore discussed. This results in protector 30 clamping about tube 21 with bag 39 between tube 21 and the inner surface of body portion 31 as seen in FIG. 5. The ring 37 extends away from body portion 31 as seen in FIG. 5 and, thus, acts as a handle to be grasped by insertion therein of the finger of the operator. Of course, any suitable handle may be provided. In fact, any means, such as stem or extension portion 36, or part thereof, alone attached to body portion 31 may be used sufficient in size to be grasped by the operator.

Figure 6:
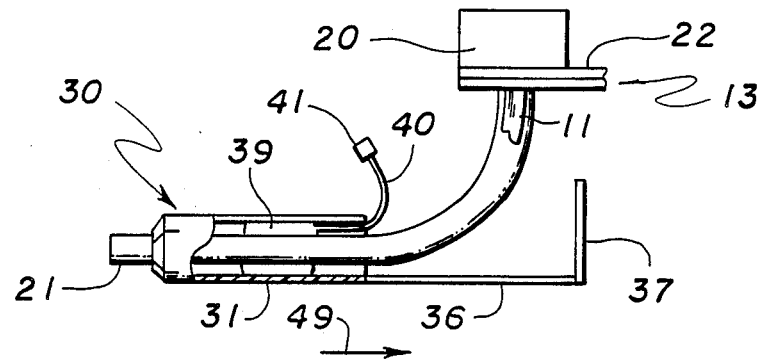
FIG. 6 is a view of a portion of the apparatus of FIG. 1 with the protector installed on the tube shown in a partially withdrawn position.

Referring to FIG. 6, syringe 17 of FIG. 1 has been removed and tracheal tube 21 has been inserted into the apparatus of FIG. 1 as set up in FIG. 5. That is, tube 21 (FIG. 5) has been inserted through holder 13, with protector 30 disposd therein as seen in FIG. 5, between needle halves 11, 12 (only a portion of needle half 11 shown in FIG. 6) and tube 21 inserted into the patient until it reaches a predetermined level. At this point, the needle halves 11, 12 may be removed and ring 37 is grasped and the protector 30 is pulled off of tube 21 in the direction of arrow 49 in FIG. 6. That is, protector 30 again separates along line 34 and slits 45 to 48, slides over tube 21 and is removed therefrom while the terminal end of tube 21 remains in the patient to the aforementioned predetermined depth.

The bag 39 can now be inflated by connection of a syringe to connector 41 as heretofore discussed.

Obviously, protector 30 can be used when inserting tracheal tube 21 through an incised area or through instrumentation, or both, as heretofore discussed and removed before or after removal of needle halves 11, 12. Any suitable materials may be used but plastic material with a memory after molding is preferred. The protector slips easily over tracheal tubes of varying outer diameters, such as adult tracheal tubes of varying outer diameters, such as adult tracheal tubes between 7 to 12 mm in diameter (outer), with bags glued thereto.

The protector 30 protects the bag 39 from breakage or piercing of the same due to its engagement with sharp edges or elements of the instrumentation or sharp edges of cartilage of the patient.

The protector is not only quickly and easily installed on the tube, but easily inserted through the instrumentation and/or into the patient along with the tube until the desired depth is reached, then quickly and easily removed leaving the tube in place. It can then be reused or discarded since such protector may be quite inexpensive.

Of course, any suitable means may be used to carry out the foregoing and the invention herein is to be limited only by the appended claims.

I claim:

1. Apparatus for preventing breakage of bags of tracheal tubes comprising:
   an elongated resilient hollow tracheal tube having a terminal end and a central longitudinal axis, a normally deflated inflatable bag surrounding a portion of said tube adjacent the terminal end thereof and secured thereto, an elongated inlet tube coupled thereto in fluid communication with said bag;
   a protector having a tubular body portion with a forward end and rear end, said tubular body portion surrounding said bag and the portion of said tube surrounded by and adjacent to said bag with said bag entirely contained within said tubular body portion of the protector, said tubular body portion being of a resilient material and having an end to end slit for separation thereat to accommodate insertion of said tracheal tube and deflated bag therein, said tubular body portion of said protector being open at the forward and rear ends and having an extension portion extending away from the rear end of said body portion of said protector in a direction away from the terminal end of said tracheal tube, the forward end of said tubular body portion including a convex nose generally transverse thereacross, said nose having a restricted opening located centrally therein out of which the terminal end of said tracheal tube extends, said nose engaging about the tracheal tube inward of the terminal end and forward of the inflatable bag to protectively enclose said bag, and a plurality of spaced slits through said nose extending radially outwardly from said restricted opening for a selective spreading of said nose for retraction of the tubular body portion over said bag.

2. In the apparatus of claim 1 wherein said extension portion terminates in a handle portion.

3. In the apparatus of claim 2 wherein said handle portion is a ring.

4. In the apparatus of claim 3 wherein said ring is longitudinally aligned with said restricted opening.

5. In the apparatus of claim 4 wherein said protector is a molded piece of material.

6. In the apparatus of claim 6 wherein said protector is of polyethylene material.

7. In the apparatus of claim 1 wherein said protector body portion is generally cylindrical with a generally cylindrical interior.

8. A protector adapted to surround a tracheal tube and protect a bag surrounding and secured to the same, the protector comprising:

an elongated tubular body portion with a forward end and rear end, and having a central longitudinal axis, said tubular body portion being of a resilient material and having an end to end slit for separation thereat, said body portion being open at both ends and having an extension portion extending away from the rear end of said body portion, the forward end of said body portion comprising a nose, said nose being convex and disposed generally normal to the longitudinal axis of said body portion and having a restricted opening located centrally therein, said central longitudinal axis extending through said restricted opening, a plurality of spaced slits through said nose extending radially outwardly from said restricted opening for a selective spreading of the nose and an enlargement of the restricted opening.

9. In the protector of claim 8 wherein said extension portion terminates in a handle portion.

10. In the protector of claim 9 wherein said handle portion is a ring.

11. In the protector of claim 10 wherein said ring is longitudinally aligned with said restricted opening.

12. In the protector of claim 13 wherein said protector is a molded unitary piece of material.

13. In the protector of claim 12 wherein said protector is of polyethylene material.

14. In the protector of claim 8 wherein said body portion is generally cylindrical with a generally cylindrical interior.

* * * * *